United States Patent [19]

Ferrante et al.

[11] Patent Number: 5,604,258
[45] Date of Patent: Feb. 18, 1997

[54] METHODS FOR TREATING MALARIA AND OTHER DISEASES

[75] Inventors: Antonio Ferrante, Mt. Osmond; Alfred Poulos, Kensington Gardens; Lakshmi M. Kumaratilake, Piccadilly; Brenton S. Robinson, Kingswood, all of Australia

[73] Assignee: Women's and Children's Hospital Adelaide, North Adelaide, Australia

[21] Appl. No.: 170,176

[22] PCT Filed: Jun. 24, 1992

[86] PCT No.: PCT/AU92/00313

§ 371 Date: Mar. 14, 1994

§ 102(e) Date: Mar. 14, 1994

[87] PCT Pub. No.: WO93/00084

PCT Pub. Date: Jan. 7, 1993

[30] Foreign Application Priority Data

Jun. 24, 1991 [AU] Australia .................. PK6830

[51] Int. Cl.⁶ ........................................ A61K 31/20
[52] U.S. Cl. ............................................... 514/560
[58] Field of Search ................................ 514/560

[56] References Cited

U.S. PATENT DOCUMENTS 4,997,851  3/1991  Isaacs et al. ................. 514/558

FOREIGN PATENT DOCUMENTS

0465423A2  1/1992  European Pat. Off. .
0468441A1  1/1992  European Pat. Off. .
WO90/15609  12/1990  WIPO .

OTHER PUBLICATIONS

Paul T. Fawcett et al. "Effects of an eicosapentaenoic acid . . . " Arthritis Rheum. vol. 32 No. 4SUP, 1989, p. S38.
P. T. Fawcett et al. "Virulent murine malaria: enhanced survival . . . " Clinical Research, vol. 32 No. 5, 1984, p. 847A.
O. A. Levander et al. "Comparative antimalarial effects of N–3 . . . " FASEB J., vol. 5 No. 5, 1991, p. A1080.

*Primary Examiner*—Phyllis G. Spivack
*Attorney, Agent, or Firm*—Nixon & Vanderhye

[57] ABSTRACT

Methods for treating melanoma or a disease caused by bacteria, fungi, Chlamydia, Mycoplasma, Rickettsia or *Plasmodium falciparum* are disclosed wherein a fatty acid having a carbon length up to 30 carbon atoms and two or more double and/or triple bonds, derivatives or oxidation products thereof is administered.

26 Claims, 10 Drawing Sheets

Fig. 2 cis - configuration trans - configuration

METHODS FOR TREATING MALARIA AND OTHER DISEASES

This application is a 371 of PCT/AU92/00313 filed Jun. 24, 1992 and published a WO93/00084 Jan. 7, 1993.

BACKGROUND TO THE INVENTION

Over half of the world's population, in some 100 countries, is at risk from malaria, with about 500 million acute infections and approximately 1 million deaths recorded each year (1, 2). As a whole, the situation with respect to this disease has shown little improvement in the last 15 years. Vaccine development is proving lengthy and complex and, at the present time, there is no completely satisfactory vaccine on the market. The use of antimalarial drugs still causes major problems due to widespread drug resistance and the toxicity related effects of present chemotherapy.

We have now identified a group of compounds which can induce killing of malaria and other parasites, bacteria, viruses, fungi and tumors. These compounds are non-toxic, and it is unlikely that disease organisms will be able to develop resistance to them.

SUMMARY OF THE INVENTION

According to the present invention, there is provided a pharmaceutical or veterinary composition, for the prevention or treatment of malaria and other diseases (as described below), comprising a polyunsaturated fatty acid, a derivative thereof or oxidation product in a pharmaceutically or veterinarily acceptable vehicle.

According to a further aspect of the invention, there is provided a dietary supplement, for the prevention or treatment of malaria and other diseases (as described below), comprising a polyunsaturated fatty acid, a derivative thereof or oxidation product in an edible vehicle.

According to a yet further aspect of this invention, there is provided a method of prevention or treatment of malaria or other diseases (as described below), comprising the administration of a polyunsaturated fatty acid, a derivative thereof or oxidation product, either by itself or in the form of a dietary supplement or a pharmaceutical or veterinary composition (as described above).

The term "polyunsaturated fatty acid", as used throughout the specification and claims, is defined as being a fatty acid comprising two or more double and/or triple bonds. That is, the fatty acid may comprise double bonds only, triple bonds only or a combination of double and triple bonds. Preferably, the fatty acid comprises two or more double bonds, in particular, 2 to 6 double bonds.

NON-SPECIFIC IMMUNITY

The term "non-specific immunity" is defined as the ability of the host defence system to utilize components of the body which do not require specific recognition factors such as antibodies and cytotoxic T lymphocytes. Previously identified mediators of non-specific immunity constitute a range of different kinds of factors, including oxygen-derived reactive species, aminoaldehydes, cytokines and various other factors (at present, incompletely characterized) in the serum of hosts showing non-specific resistance to disease. These non-specific defence mechanisms play a valuable role in defence against infection and malignant diseases. Non-specific immunity acts as a defence against infection by such agents as bacteria, fungi, parasites and viruses, and also as a defence against tumors.

In vivo correlates of non-specific immunity, resulting from the injection of stimulators of non-specific immunity, are: (a) activated macrophages which non-specifically kill bacteria, fungi, parasites, virus-infected cells and tumor cells and (b) the appearance of tumor necrosis serum (TNS) in hosts. TNS has been shown to induce death of parasites and tumor cells.

Despite an extensive interest in mediators of non-specific immunity over the last 30 years, there have been few breakthroughs regarding further candidates which could be potential mediators of non-specific immunity.

We have now surprisingly discovered that polyunsaturated fatty acids, derivatives thereof and oxidation products are mediators of non-specific immunity.

COMPOUNDS OF THE PRESENT INVENTION

The compounds used in the present invention are polyunsaturated fatty acids (PUFA), derivatives thereof and oxidation products. Many of these compounds are naturally-occurring, and known to be non-toxic to warm-blooded animals.

Preferred compounds are n-1 to n-10 PUFA, especially n-3 to n-6 PUFA, and in particular n-3 and n-6 PUFA. The numbering "n-1" etc indicates the position of the first double bond in the fatty acid molecule, counting from the end of the molecule distal from the carboxyl group.

Suitable derivatives are esters, preferably $C_{1-6}$ esters and, in particular, methyl or ethyl esters; alcohols and amides.

Oxidation products include hydroxy fatty acids, hydroxy alkanals, hydroperoxy and endoperoxide derivatives, malonaldehyde and malondialdehyde.

Figure 1A:
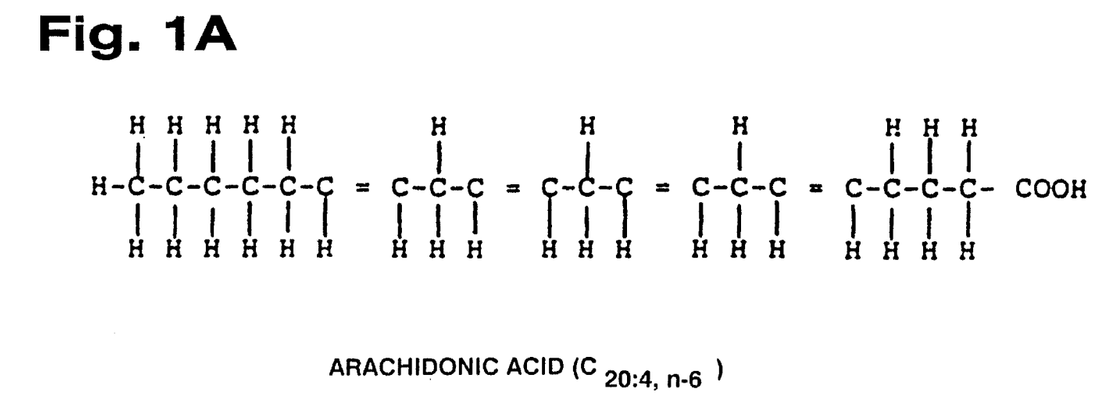
FIGS. 1A and 1B and 2 illustrate the nomenclature used with respect to the compounds of the present invention.
Figure 1B:
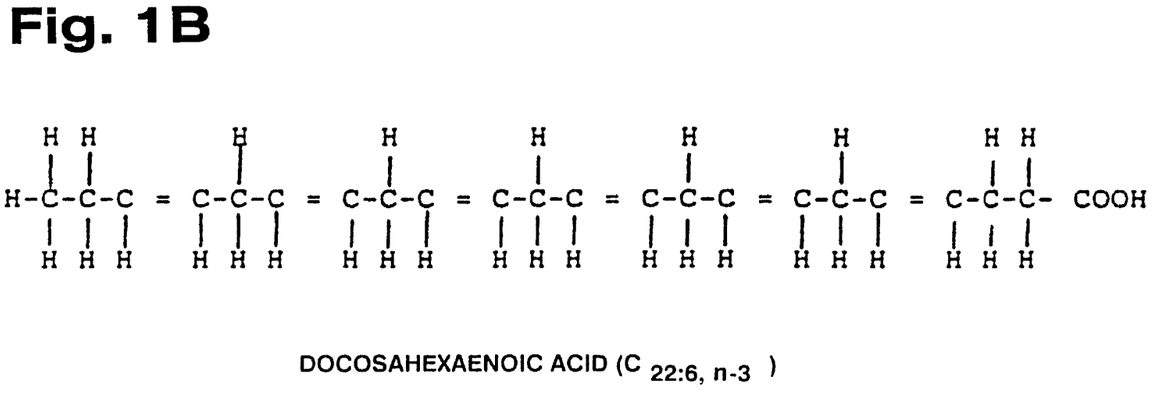
Figure 2:
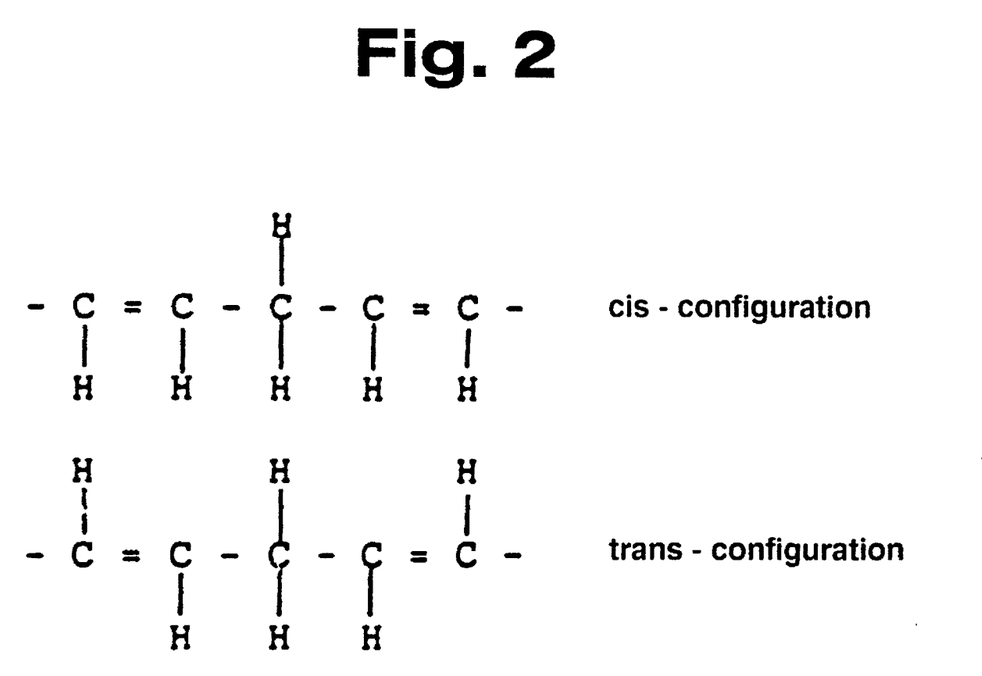

PUFA, wherein the double bonds are methylene-interrupted (eg the compounds illustrated in FIG. 1) and/or have a cis configuration (see FIG. 2), have been found to be particularly effective. It is probable that trans conformation PUFA will have the same effect.

Most naturally-occurring PUFA found in animals and plants are n-3 and n-6 derivatives. The n-3 series PUFA are found in particularly high concentrations in marine animals. In the n-3 series, the double bond closest to the omega-end of the molecule (ie furthest from the carboxyl group) is located between the 3rd and 4th carbon atoms (counting the terminal methyl carbon atom as 1). In the n-6 series, the double bond closest to the omega-end of the molecule is located between the 6th and 7th carbon atoms.

The carbon chain length of the PUFA of the present invention may vary significantly, and can be as high as 30 carbon atoms. The preferred PUFA of the present invention are naturally-occurring PUFA having 15 to 25 carbon atoms, in particular 18, 20 or 22 carbon atoms, such as linolenic acid, arachidonic acid, eicosapentaenoic acid and docosahexaenoic acid.

THERAPEUTIC ACTIVITY

PUFA, their derivatives and their oxidation products are effective in killing a wide range of bacteria, fungi, protozoan and helminth parasites, inhibiting replication of viruses, and killing tumor cells.

In particular, the compounds of the present invention may be effective in treating or preventing diseases caused by:

A. PROTOZOAN PARASITES

Malaria
*P. falciparum*
*P. vivax*
*P. berghei*
*P. brasilianum*

Toxoplasmosis
*T. gondii*

Trypanosomiasis
*T.b. gambiense*
*T.b. rhudesiense*
*T.b. brucei*
*T.b. congleuse*
*T.b. vivas*
*T. cruzi*
*T. musculi*

Leishmaniasis
*L. major*
*L. brazilensis*
*L. donovani*

Amoebiasis
*E. histolytica*

Trichomoniasis

Primary amoebic meningitis
*N. fowleri*

Chronic acanthamoebic encephalitis and keratitis
*A. culbertsoni*

Giardiasis
*G. intestinalis*

Babesiosis
*B. bovis*
*B. bigemina*

B. MAJOR HELMINTH PARASITES OF HUMANS

| Organism | Common Name |
|---|---|
| Nematodes | |
| *Ancylostoma duodenale* | Hookworm |
| *Ascaris lumbricoides* | Giant roundworm |
| *Enterobius vermicularis* | Pinworm |
| *Onchocerca volvulus* | River blindness |
| *Strongyloides* | Strongyloidiasis |
| *Trichinella spiralis* | Trichinosis |
| *Trichuris trichiura* | Whipworm |
| *Wuchereria bancrofti* | Filariasis |
| Trematodes | |
| *Clonorchis sinensis* | Liver fluke |
| *Fasciola hepatica* | Liver fluke |
| *Fasciolopsis buski* | Intestinal fluke |
| *Paragonimus westermani* | Lung fluke |
| *Schistosoma haematobium* | Blood fluke |
| *Schistosoma japonicum* | Blood fluke |
| *Schistosoma mansoni* | Blood fluke |
| Cestodes | |
| *Diphyllobothrium latum* | Fish tapeworm |
| *Taenia saginata* | Beef tapeworm |
| *Taenia sodium* | Pork tapeworm |
| *Echinococcus granulosus* | Hydatid cyst |

PUFA, their derivatives and oxidation products have broadspectrum antibacterial activity against gram-positive cocci, gram-positive bacilli, gram-negative cocci, gram-negative bacilli, spirochetes, anaerobic bacteria and mycobacteria. Therefore, they can be used therapeutically in combatting diseases caused by such organisms.

The compounds of the present invention are also fungicidal and fungistatic against *Candida albicans, Cryptococcus neoformans, Histoplasma capsulatum, Aspergillus fumigatus* and *Pneumocystis carinii*. Accordingly, they are effective in preventing or treating mycotic diseases.

PUFA, their derivatives and oxidation products are also active as antiviral agents. The fatty acids interact with the virus-infected host cell and may either induce changes in the cell which inhibit viral replication or, at higher concentration, damage the virus-infected host cell. This makes the PUFA, such as $C_{22:6}$ or its hydroxy form, suitable as broadspectrum antiviral agents. They are effective against diseases caused by the DNA viruses: Poxviridae, Herpesviridae, Adenoviridae, Papoviridae, Hepadnaviridae and Parvoviridae, as well as against diseases caused by the RNA viruses: Reoviridae, Togaviridae, Flaviviridae, Coronaviridae, Paramyxoviridae, Rhabdoviridae, Filoviridae, Orthomyxoviridae, Bunyaviridae, Arenaviridae, Retroviridae, Picornaviridae and Caliciviridae.

The compounds of the present invention are effective in inhibiting the growth of *Chlamydia, Mycoplasma* and *Rickettsia*. These compounds are therefore agents against chlamydial diseases, mycoplasma diseases and rickettsiosis.

PUFA, their derivatives and oxidation products also have antitumor properties.

EXAMPLES

The following Examples are intended to further illustrate the present invention, and are not intended to limit the scope of the invention in any way.

EXAMPLE 1

ACTIVITY AGAINST *PLASMODIUM FALCIPARUM*

Parasite. Six isolates of *Plasmodium falciparum* (knob positive and negative) were maintained under in vitro conditions in Group $O^+$ human red blood cells (RBC) in RPMI 1640 medium (Cytosystems Pty Ltd, New South Wales, Australia) supplemented with 10% heat inactivated Group $AB^+$ serum as, described previously (3, 4). Experiments were performed with synchronized and non-synchronized cultures at $10^8$ RBC/ml with 3–5% parasitaemia.

Fatty acids.

Docosahexaenoic acid ($C_{22:6, n-3}$), docosahexaenoic acid methyl ester ($C_{22:6, n-3}$ methyl ester), eicosapentaenoic acid ($C_{20:5, n-3}$), arachidonic acid ($C_{20:4, n-6}$), linoleic acid ($C_{18:2, n-6}$), oleic acid ($C_{18:1, n-9}$), docosanoic acid ($C_{22:0}$) and Dl-α-dipalmitoyl phosphatidylcholine (DP-PC) were obtained from Sigma Chemical Co, St Louis, Mo., USA. Lipids were dissolved in redistilled chloroform (10–50 mg/5 ml) and stored under $N_2$ at –20° C. Thin layer chromatography indicated that the lipids were of high purity. Mixed fatty acid/DP-PC micelles were prepared as follows: Fatty acid (8,32 or 80 μg) and DP-PC (4-fold the amount of fatty acid) were dispensed into 10 ml glass tubes and the solvent evaporated under $N_2$. RPMI 1640 medium (2 ml) was added and the mixture sonicated for 2 minutes with an ultrasonic processor (model W-225; Heat Systems—Ultrasonics, Inc, Farmingdale, N.Y., USA) with 40% duty cycle and output setting 4. The lipid sonicares were clear under these conditions. Aliquots (50 μl) of each sonicate (containing 4,16 or 40 μg/ml fatty acid) were used for assays unless stated otherwise.

Growth Inhibition Assay.

Figure 3:
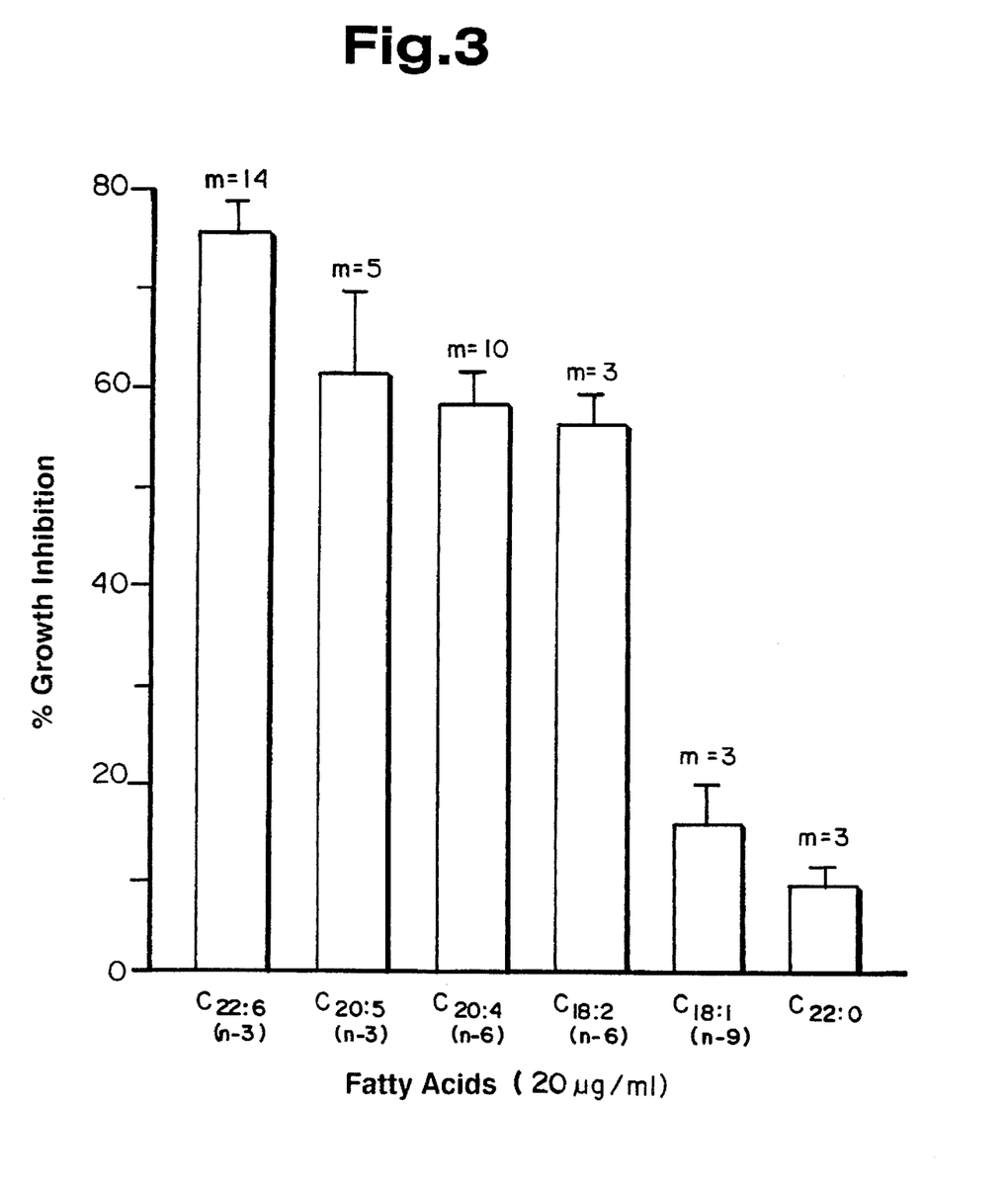
FIG. 3 illustrates the effects of various fatty acids on *Plasmodium falctparum*.

This was carried out as described previously (3, 4), with the following modifications. Experiments were conducted in 96 well flat-bottomed microdilution plates (Linbro, Flow Laboratories, Inc, McLean, Va.), comparing three different treatment groups. Fifty microlitres of *P. falciparum*-infected RBC ($1 \times 10^8$/ml, 2–5% parasitaemia) were mixed with 50 μl of either fatty acids (40 μg/ml), diluent (DP-PC) or malaria medium. The plates were incubated for 2 h at 37° C. in 5% $CO_2$ in air. Then the wells were pulsed with 1μCi cf [$^3$H] hypoxanthine (Amersham Corp, Arlington Heights, Ill.) in 50 μl RPMI 1640 medium and incubated for a further 18 h at 37° C. in 5% $CO_2$ air. Individual well contents were then collected using a semi-automated sample harvester (Titertek, Flow Laboratories, NSW, Australia), and the [$^3$H] hypoxanthine incorporation was measured by a liquid scintillation counter (Beckman model, LS 3801). Percent growth inhibition of the parasite was calculated by the following formula: Percent inhibition={(dpm of parasite in diluent)—(dpm of parasite incubated with fatty acids)×100}/(dpm of parasite in diluent), where dpm=disintegrations per minute. The results of this assay are illustrated in FIG. 3.

A. Effects of fatty acids and fatty acid structure on growth inhibition. FIG. 3 summarizes the effects of fatty acids and fatty acid structure on the growth of *P. falciparum*. The symbol m indicates the number of different experiments carried out with each fatty acid. Treatment of parasites with $C_{22:6, n-3}$, $C_{20:5, n-3}$, $C_{20:4, n-6}$ and $C_{18:2, n-6}$ fatty acids resulted in marked inhibition of *P. falciparum* growth, which was significantly higher than the effects of $C_{18:1, n-9}$ and $C_{22:0}$. The highest anti-malarial activity was always seen with $C_{22:6, n-3}$ (76%±3.3 growth inhibition). The methyl ester of this fatty acid was just as effective (71%±4.3). Similar results were obtained when fatty acids were delivered in either albumin or DP-PC (data not shown on FIG. 3).

Figure 4:
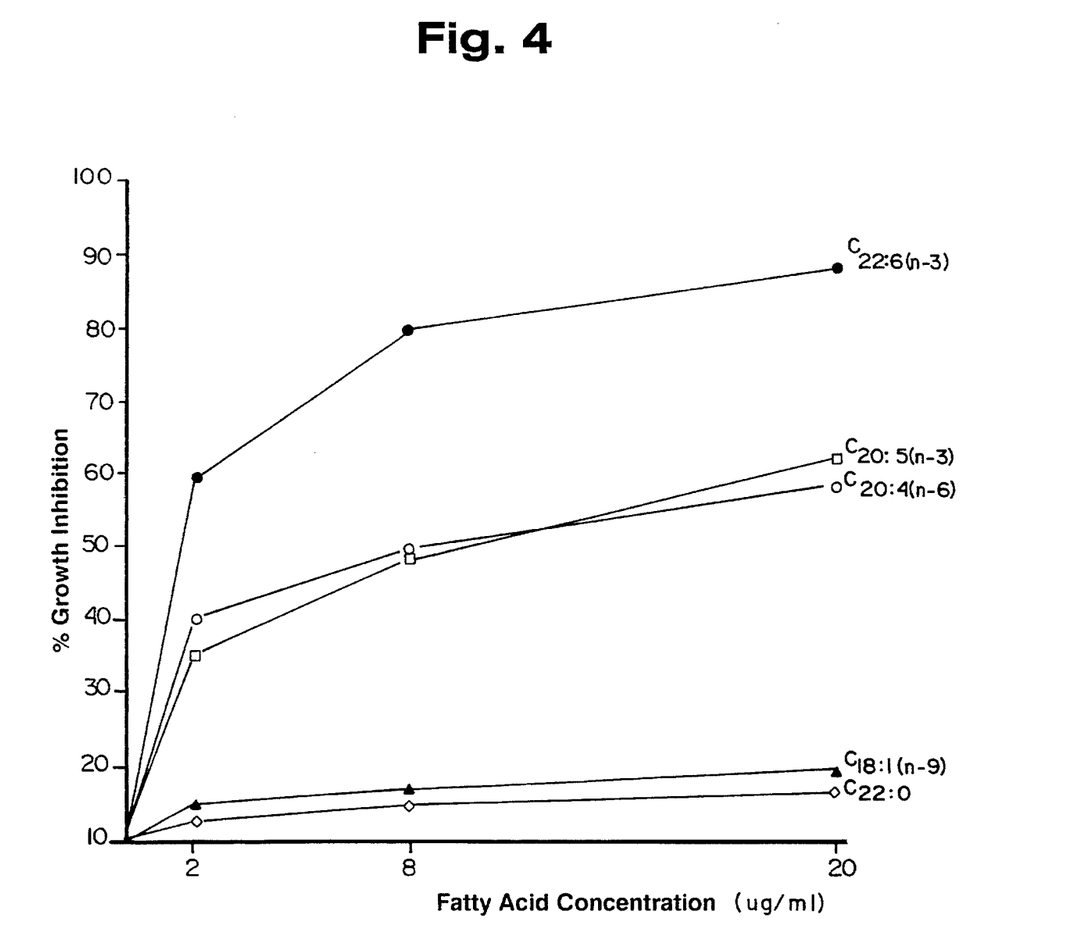
FIG. 4 illustrates the concentration related anti-*P. falciparum* activity of fatty acids.

The anti-malarial activity of the fatty acids was concentration-dependent (FIG. 4). Within the range of 4–40 μg/ml, the fatty acids did not induce haemolysis of parasitized or normal RBC, as assessed by haemoglobin release and by morphological criteria. At these concentrations, DP-PC was not toxic to *P. falciparum* and [$^3$H] hypoxanthine incorporation was not affected by the presence of the phospholipid.

Figure 8A:
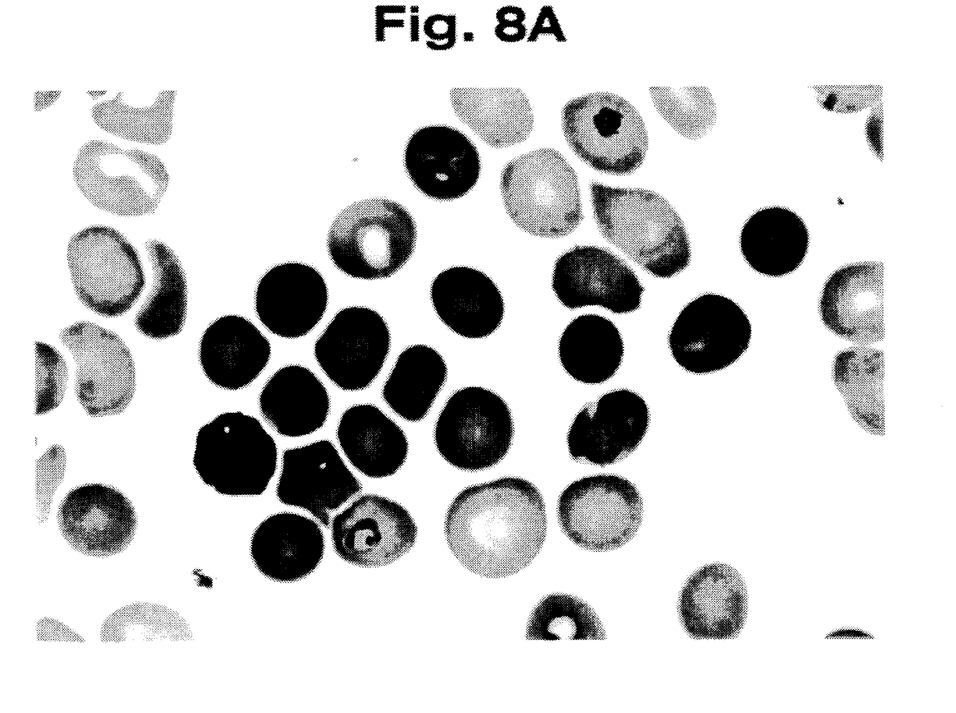
FIGS. 8A and 8B illustrate the effect of $C_{22:6, n-3}$ fatty acid on the morphology of *P. falciparum* infected human red blood cells (RBC)
Figure 8B:
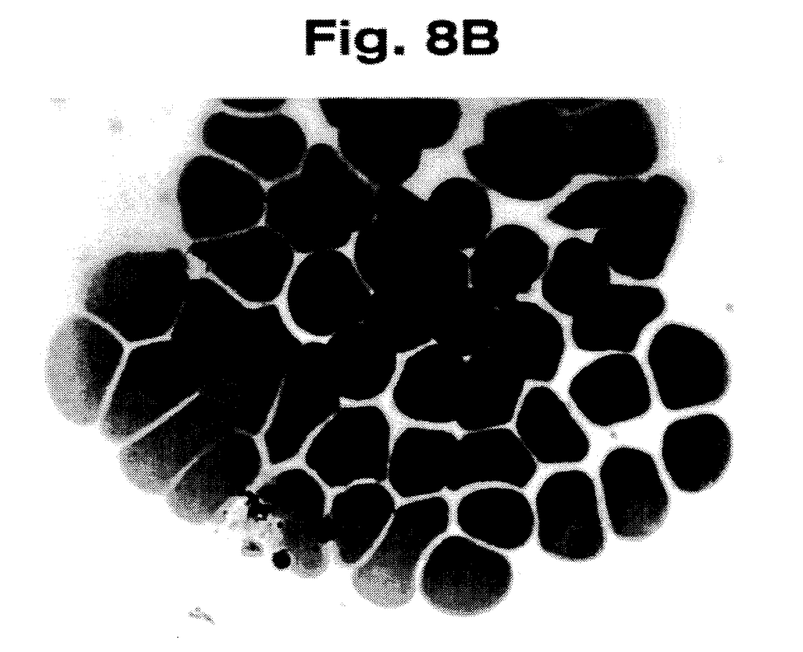

Microscopic examination revealed that parasites exposed to fatty acids for 18 h underwent degeneration and death (FIG. 8). FIG. 8A illustrates the normal morphology of *P. falciparum* infected RBC, showing various stages of maturation. FIG. 8B illustrates the same culture incubated with $C_{22:6, n-3}$ for 18 h. (Note: The cytoplasm does not absorb Giemsa stain, the nucleus is darkly stained and condensed, and the parasites are devoid of any normal structures.) It appeared that immature and mature schizonts were more susceptible to the fatty acid-induced effects than were the ring forms. However, the majority of ring forms were also found to be degenerated. Different fatty acids had different effects. For example, $C_{22:6, n-3}$ caused >90% death of *P. falciparum*. Almost all of the surviving parasites (10% parasitaemia) were in the ring form. $C_{20:4, n-6}$ caused 80% death or degeneration of the parasite. In addition to rings, a small percentage of schizonts also survived, but their cytoplasm did not stain with Giemsa and the nuclei were dense and darkly stained, with a parasitaemia of 15% With $C_{20:4, n-6}$, approximately 15% mature schizonts and 70% immature schizonts showed abnormalities. By way of contrast, $C_{22:0}$-treated *P. falciparum* cultures were very similar to the parasite grown in the absence of fatty acids.

Figure 5:
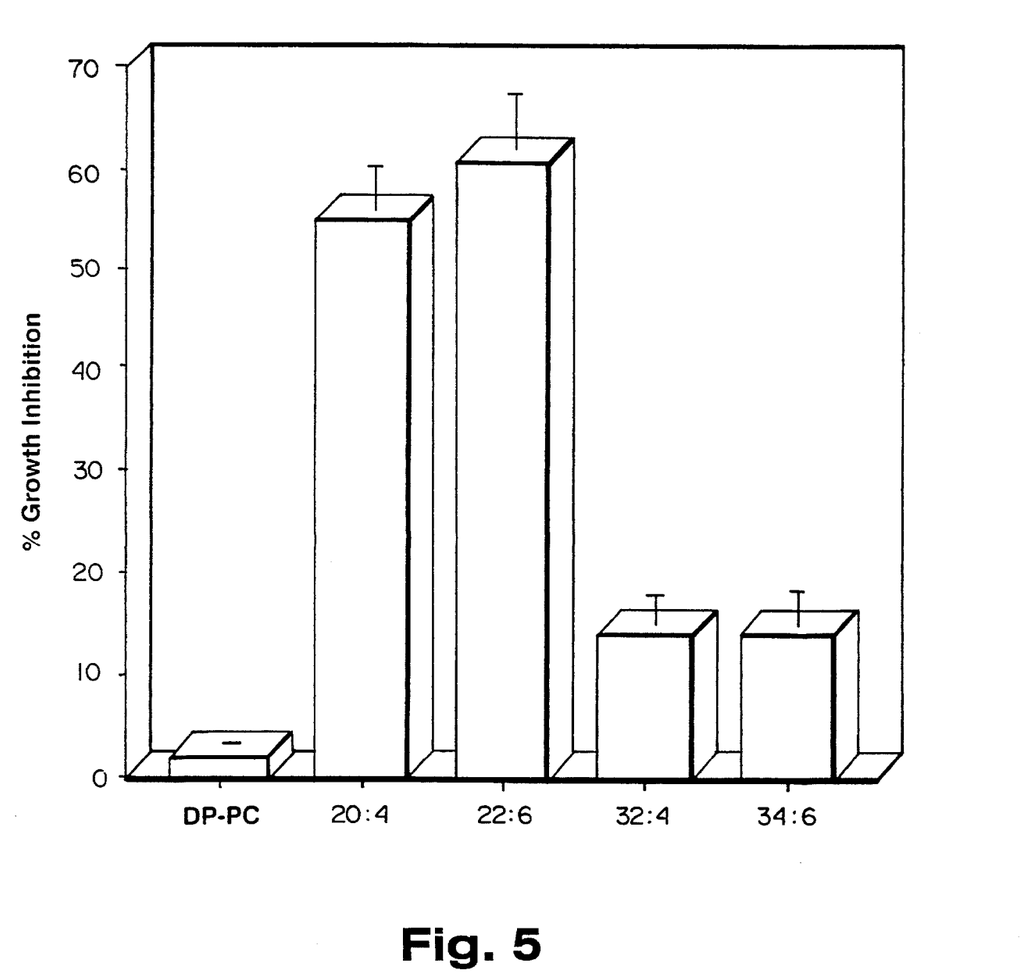
FIG. 5 illustrates the effects of increasing the carbon chain length of the fatty acid.

FIG. 5 illustrates the effect of increasing the carbon chain length on the anti-malarial activity of PUFA. $C_{32:4}$ and $C_{34:6}$ are far less effective than $C_{20:4}$ and $C_{22:6}$, respectively. Increasing the carbon chain length, whilst maintaining the same number of double bonds, leads to decreased activity, particularly if the number of carbon atoms is greater than 30.

B. Effects of fish oil on growth of *P. falciparum*. Using the growth inhibition assay described above, the effects of fish oil (MAXEPA, Duncan, Flockhart, UK) containing the triglycerides of 18% w/w $C_{20:5, n-3}$ fatty acid and 12% w/w of $C_{22:6, n-3}$ fatty acid were tested. Fifty μl of fish oil at concentrations of 4, 16, 20 and 40 μg/ml incorporated into DP-PC were added to 50 μl of RBC with 3–5% parasitaemia. The effects of fish oil were studied after 2 h and 20 h incubation with parasitized with RBC (PRBC), before addition of [$^3$H] hypoxanthine.

Fish oil (40 μg/ml) showed a low inhibition of the parasite. When fish oil at 40 mg/ml was interacted with PRBC for 2 h, the parasite inhibition was 20.5%±8.5. However, when the interaction time was increased to 20 h, an increased parasite inhibition (41.0%±5.5) was observed.

C. Effects of oxidized fatty acids and anti-oxidants on growth of P. falciparum. $C_{22:6, n-3}$ and $C_{20:4, n-6}$ fatty acids were dispensed into 10 ml glass tubes and the solvent was evaporated under $N_2$. The dried residues were auto-oxidized by exposure to the air at room temperature for 2–4 days. Thin-layer chromatography indicated that more than 95% of the parent fatty acids had been oxidized by this procedure. Products included monohydroperoxy derivatives and other more polar oxygenated compounds (5). These oxidized fatty acids were compared with freshly prepared fatty acids using the standard radiometric growth inhibition assay.

The effects of anti-oxidants, catalase and superoxide dismutase (SOD) on the interaction of *P. falciparum* and fatty acids were examined. PRBC (500 μl) were mixed with equal volumes of the following: (i) butylated hydroxytoluene (BHT) (Sigma) 60 μM in 0.5% ethanol, (ii) DL-α-tocopherol (Vitamin E) 40 μM in 0.5% ethanol, (iii) superoxide dismutase (SOD) from bovine RBC (Sigma) 1 mg/ml, (iv) catalase from bovine liver (Sigma) 1 mg/ml, (v) 0.5% ethanol (diluent of BHT and vitamin E) and (vi) malaria medium, in an 18 well microdilution plate (Linbro, Flow Laboratories, Inc, McLean, Va.), and incubated for 18 h in a candle jar at 37° C. (6). Following incubation, blood smears were prepared, stained and parasitaemias determined. The well contents were centrifuged, the supernatant was replaced with an equal volume of malaria medium or with medium comprising antioxidants, catalase and SOD; and the PRBC pellet was resuspended. PRBC were dispensed into 96 well microdilution plates, reacted with the fatty acids $C_{22:6\ n-3}$ and $C_{20:4,\ n-6}$ for 2 hours and parasite growth inhibition was studied using the standard radiometric assay described above.

Figure 6:
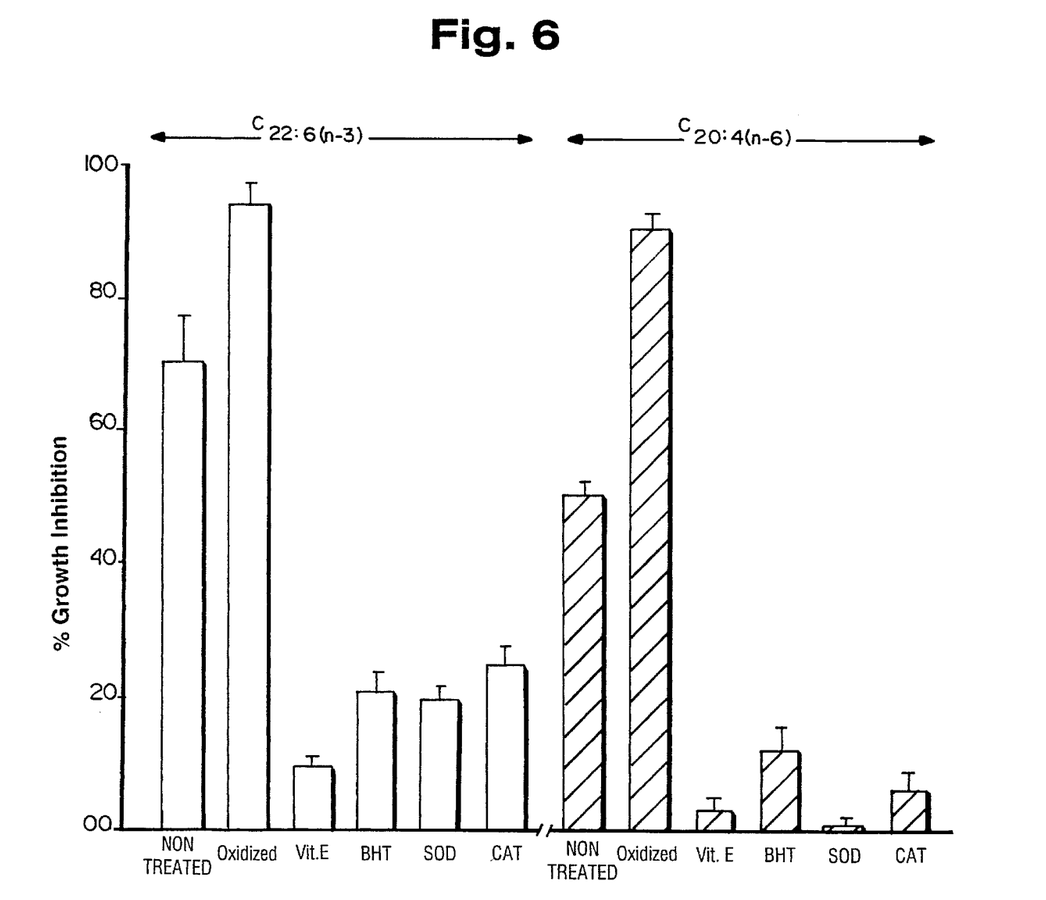
FIG. 6 illustrates the effects of oxidation of fatty acids on their ability to damage *P. falctparum*.

The oxidized forms of these fatty acids showed increased and $C_{20:4,\ n-6}$ showed significantly more anti-parasitic activity against *P. falciparum* (FIG. 6). Oxidized $C_{22:6,\ n-3}$ activity ($P<0.01$) than the non-oxidized forms (FIG. 6). The effect of pre-incubation of PRBC with anti-oxidants (Vit E—Vitamin E, BHT—butylated hydroxytoluene, SOD—superoxide dismutase and CAT—catalase) on the ability of the fatty acids to damage *P. falciparum* was also tested. Anti-parasitic effects were reduced by about 50% if PRBC were pre-incubated with BHT or Vitamin E overnight, washed and then exposed to fatty acids. Anti-parasitic activity was reduced by over 70% when the pre-incubated PRBC were reacted with fatty acids in the presence of BHT and Vitamin E (FIG. 6). The effects of fatty acids were also greatly reduced if the PRBC were treated with SOD or catalase without pre-incubation (FIG. 6). Ethanol (0.5%), the diluent for some of these reducing reagents, had no effect on parasite growth.

D. Comparison of use of albumin and DP-PC micelles to incorporate fatty acids. Mixed fatty acid/DP-PC micelles were compared with fatty acids (40 µg/ml) sonicated in the presence of 3 mg/ml fatty acid-free albumin (Sigma) by using the standard radiometric assay described above.

Similar results were obtained when fatty acids were delivered in either albumin or DP-PC, as determined morphologically and radiometrically.

As a control, self micelles of the fatty acid ($C_{22:6,\ n-3}$) were prepared and tested.

Self micelles are prepared by dispensing 75 ug of fatty acid (stock solution 10–20 mg/5 ml chloroform stored under $N_2$ at −20° C.) into a 10 ml glass tube and evaporating the solvent under $N_2$. 3 ml of 0.9% NaCl is then added and the mixture is sonicated for 3 minutes with an ultrasonic processor (model W-225; Heat Systems—Ultrasonics, Inc, Farmingdale, N.Y., USA) with output setting 4. Under these conditions, a clear lipid sonicate is produced. 400 ul aliquots of the sonicate were used for animal injections.

Figure 7:
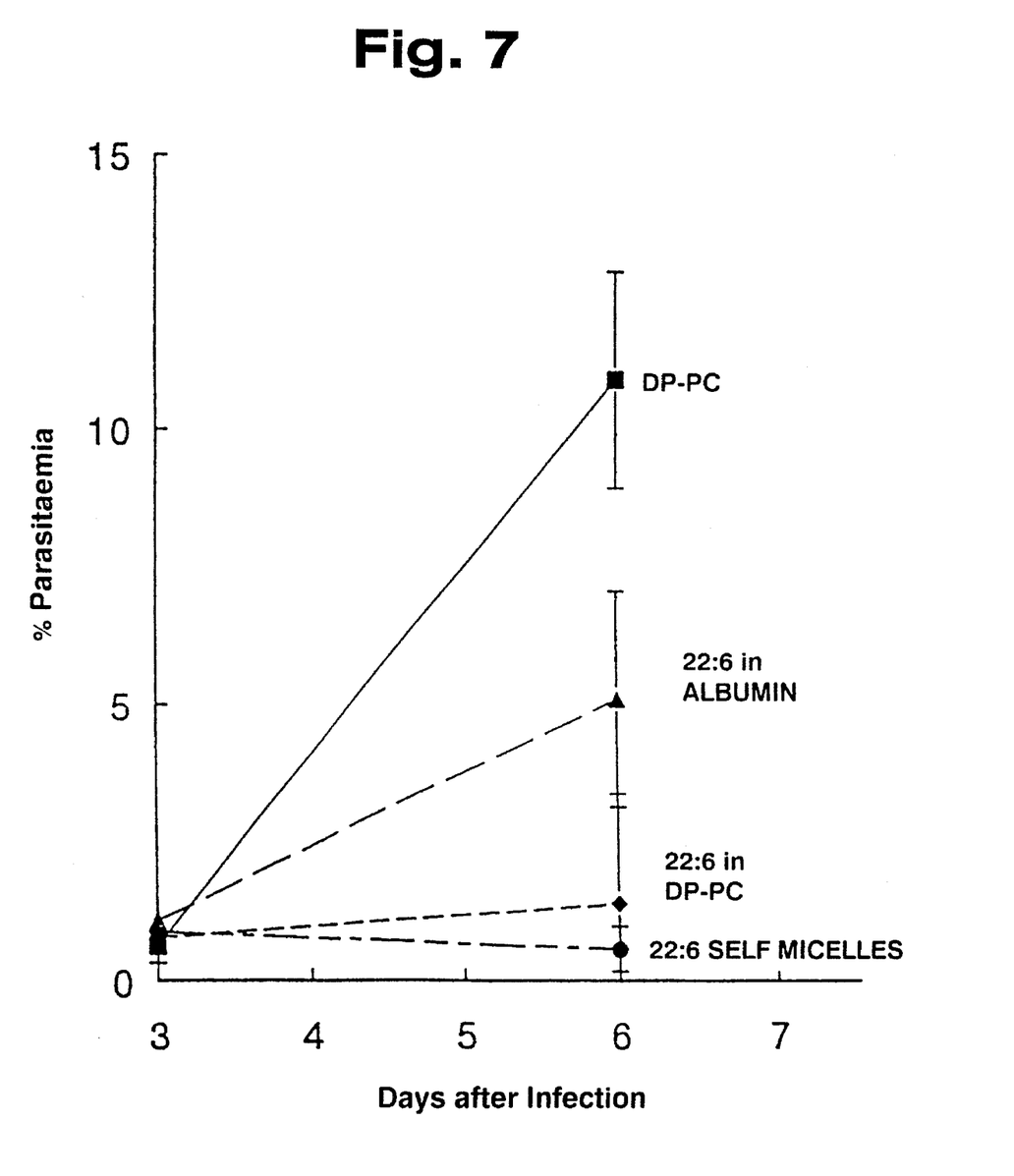
FIG. 7 illustrates the effects of incorporation of fatty acids in various diluents.

As shown in FIG. 7, self micelles were most effective in reducing parasitaemia. Mowever, mixtures of PUFA with both albumin and DP-PC also had parasitaemia-reducing effect.

EXAMPLE 2

ACTIVITY AGAINST *TRYPANOSOMA MUSCULI*

The effects of PUFA on the haematoprotozoan *T. musculi*, which is an extracellular blood parasite, are shown in Table 1 (below). Both of the fatty acids $C_{22:6}$ and $C_{20:4}$ were found to be very toxic for *T. musculi*. The saturated fatty acid $C_{22:0}$, on the other hand, had no effect on the parasite.

TABLE 1

Effect of polyunsaturated fatty acids of *Trypanosoma musculi*, in vitro

| Fatty acid | Degree of Killing |
|---|---|
| None | — |
| DP-PC (vehicle) | — |
| Arachidonic acid ($C_{20:4,\ n-6}$) | ++++ |
| Docosahexaenoic acid ($C_{22:6,\ n-3}$) | ++++ |
| Docosanoic acid ($C_{22:0}$) | — |

Parasites ($2\times10^4$/well/100 µl) were incubated with 100 µl (10 µg of fatty acid incorporated on DP-PC). After 1 h incubation, the parasites were examined. ++++ indicates >99% of parasites killed.

EXAMPLE 3

ACTIVITY AGAINST *NAEGLERIA FOWLERI*

Table 2 (below) shows the effects of PUFA on the pathogenic free-living amoeba *N. fowleri*, which is the cause of primary amoebic meningoencephalitis. The fatty acids $C_{22:6}$, $C_{20:4}$ and $C_{20:5}$ were found to be very effective in killing these amoebae. The unsaturated fatty acid $C_{22:0}$, on the other hand, had no effect on the amoebae.

TABLE 2

Effect of polyunsaturated fatty acids on *Naegleria fowleri*, in vitro

| Fatty acid | Degree of Killing |
|---|---|
| None | No effect |
| DP-PC | No effect |
| Arachidonic acid ($C_{20:4}$) | All killed |
| Docosahexaenoic acid ($C_{22:6}$) | All killed |
| Eicosapentaenoic acid ($C_{20:5}$) | All killed |
| Docosanoic acid ($C_{22:0}$) | No effect |

Using 10 g of the fatty acid per well (measurements made after 1 h).

EXAMPLE 4

IN VIVO ACTIVITY AGAINST MALARIAL INFECTIONS

Figure 9:
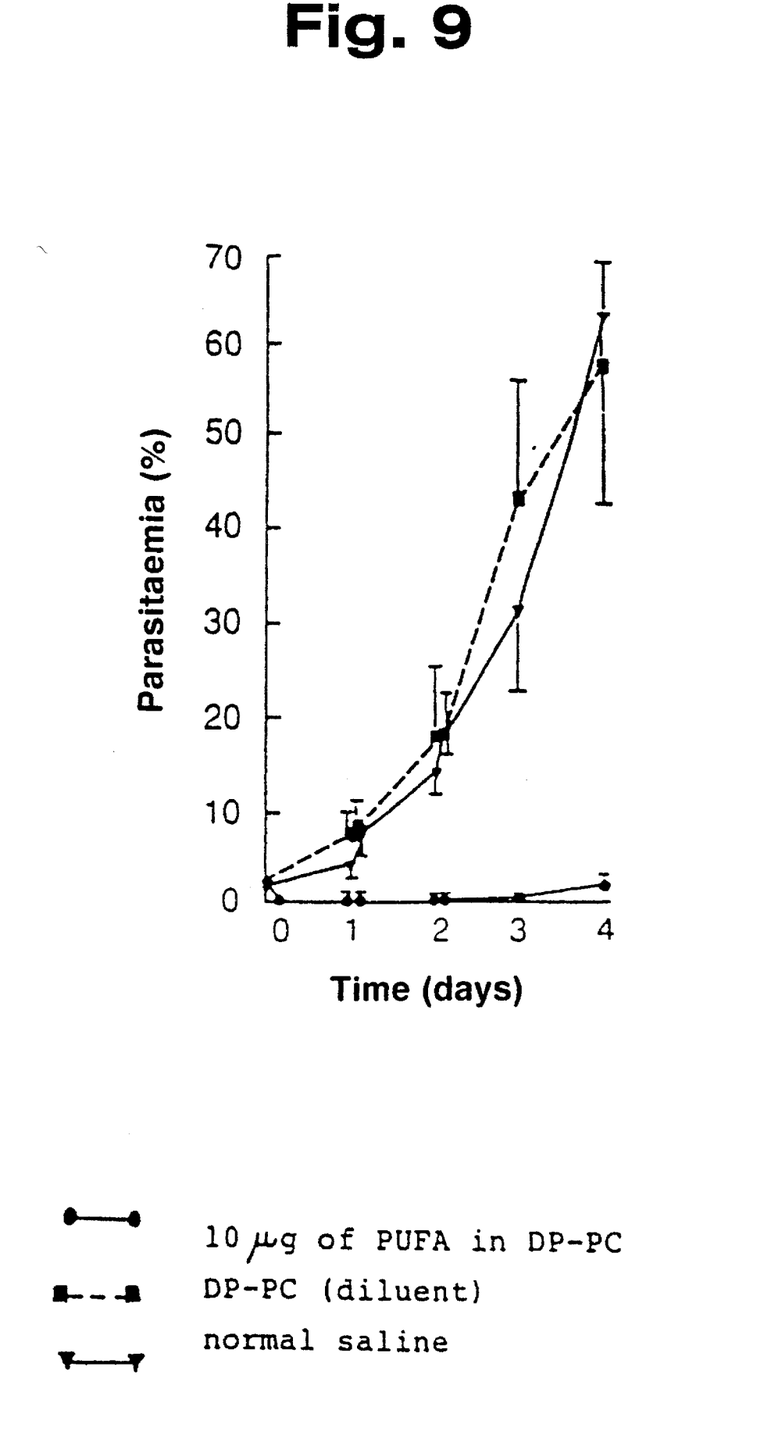
FIG. 9 illustrates the effect of $C_{22:6, n-3}$ fatty acid on *P. berghei*-infected mice.

In vivo experiments relating to the effect of PUFA, using an experimental mouse model and *Plasmodium berghei*, produced similar results to the in vitro findings with the human malarial parasite *P. falciparum* (see Example 1). BALB/c mice were infected with *P. berghei* and then, 3 days after infection, they received daily treatment of $C_{22:6,\ n-3}$ (10 µg, intraperitoneally administered). The control groups received equivalent volumes of physiological saline or an equivalent concentration of the fatty acid vehicle DP-PC. The parasitemia profiles are presented in FIG. 9 and the data shows that DP-PC had no effect on the parasite growth in mice—the levels of parasitemia were similar to those of mice that received saline. 6 days after infection, these mice showed a 60-fold increase in parasitemid (FIG. 9). After a single injection of the fatty acid $C_{22:6,\ n-3}$, the parasitemid was significantly reduced from 1.65±0.40 to 0.25±0.04% ($P<0.001$; FIG. 9). This suggests that the effect of the PUFA is directly on the parasites. Throughout the course of the treatment, the parasitemia was maintained at a lower level than the initial parasitemid (FIG. 9). Compared with the mice that received DP-PC or saline, the fatty acid-treated mice showed markedly lower parasitemia ($P<0.001$). In the mice stages. In contrast, in $C_{22:6, n-3}$-treated mice, 70–100% of treated with DP-PC or saline, the parasites grew rapidly, showing all different stages of the asexual and sexual the surviving parasites had "restricted growth" and appeared as a "dot" form. $C_{20:4, n-6}$ was similarly effective in reducing the parasitemid, but $C_{22:0}$ had no effect (data not included in FIG. 9).

On day 4, the mice were killed and the presence of anemia assessed by determining the heamatocrits. The hematocrit values for DP-PC-, saline- and $C_{22:6, n-3}$-treated groups were 26.3±2.3, 25.9±2.5 and 40.7±6.9, respectively. The results showed that the injection of $C_{22:6, n-3}$ alleviated the anemia normally associated with malarial infection. Therefore, it appears that PUFA have a secondary therapeutic effect, in that they not only kill the parasite but also act on body cells to prevent the release of mediators (cytokines), which cause the pathophysiology and the illness in malaria.

Figure 10:
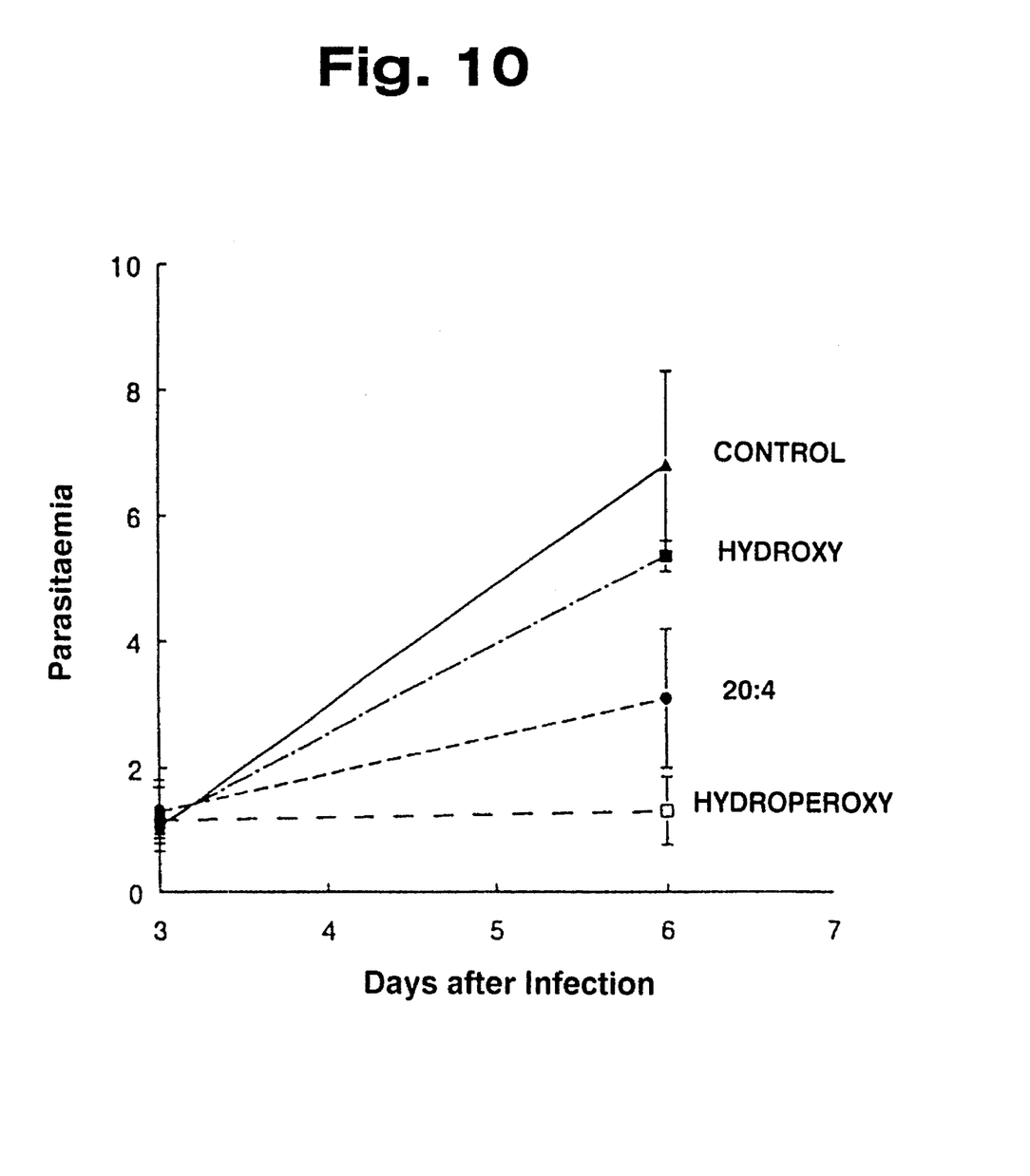
FIG. 10 illustrates the effects of oxidation products of fatty acids on *P. berghei*-infected mice.

Testing was also carried out to compare the effects of oxidation products with those of fatty acid $C_{20:4, n-6}$. Mice were injected daily (400 µg/kg body weight) with $C_{20:4, n-6}$, and its hydroxy and hydroperoxy derivatives. The results are shown in FIG. 10. The hydroperoxy derivative was the most effective.

The results of these experiments (Examples 1 to 4) were as follows:

It was established in vivo that the saturated fatty acid $C_{22:0}$ had no effect.

Arachidonic acid $C_{20:4}$ was effective, but not as effective as $C_{22:6}$.

The intraperitoneal, as well as the intravenous, routes of PUFA injection were both effective.

Use of the vehicles DP-PC and albumin, or the injection of micelles of PUFA, were all effective.

The oxidized form of the fatty acids was even more effective—namely the hydroperoxy derivative.

EXAMPLE 5

IN VITRO ACTIVITY AGAINST TUMOR CELLS

As shown in Table 3 (below), both $C_{22:6}$ and $C_{20:4}$ PUFA kill the tumor cell B16 melanoma in vitro. $C_{22:0}$ had no effect on the tumor cells.

TABLE 3

Effect of polyunsaturated fatty acids on the tumor cell B16 melanoma, in vitro

| Treatment | Microscopic examination |
|---|---|
| DP-PC | Normal healthy monolayers |
| $C_{20:4}$ | Monolayers not healthy, but some cells still attached and viable |
| $C_{22:6}$ | All cells dead and detached |
| $C_{22:0}$ | Normal healthy monolayers |

Using 10 µg of fatty acid.

DISCUSSION AND CONCLUSIONS

Example 1 above demonstrates that fatty acids caused growth inhibition of P. falciparum in culture. The polyunsaturated fatty acids belonging to the n-3 and n-6 series, in particular, caused marked growth inhibition of the parasites. These included $C_{22:6, n-3}$, $C_{20:5, n-3}$, $C_{20:4, n-6}$ and $C_{18:2, n-6}$ fatty acids. However, monounsaturated and saturated fatty acids e.g. $C_{18:1, n-9}$ and $C_{22}$ had little effect. This result demonstrates that the degree of antiplasmodial activity of the fatty acids is dependent in part on the degree of unsaturation (number of double bonds present). For example, the degree of inhibition for 22 carbon fatty acids is increased several-fold by the introduction of six double bonds into the molecule.. Similarly, the introduction of one further double bond into the monounsaturated fatty acid oleic acid ($C_{18:1, n-9}$), more than tripled the parasiticidal effects (FIG. 3).

At the concentrations tested, the fatty acids did not appear to be toxic to PRBC and normal RBC and did not induce haemolysis (determined biochemically). The diluents DP-PC and albumin had no toxic effects either on the parasite or RBC. Similar results were observed between the fatty acids prepared in either DP-PC or albumin, indicating that the results were not changed because of the agent used to dissolve the fatty acids. This is of significance since, in the body, the fatty acids bind to albumin.

Results of the in vivo experiments (Example 4) confirmed the antiplasmodial effects of the PUFA. The PUFA $C_{22:6, n-3}$ and $C_{20:4, n-6}$ were capable of inhibiting the growth of P. berghei in mice, but the saturated fatty acid $C_{22:0}$ had no effect. Importantly, the PUFA showed no toxic effects in mice but, in fact, prevented malaria-induced anemia.

Morphological studies confirmed the results obtained from the radiometric assay and clearly showed that fatty acids caused intraerythrocytic degeneration and death of P. falciparum.

PUFA are taken up with great avidity by malarial parasites, which have an absolute requirement for host fatty acids because of inability to synthesise these lipids.

The mechanism behind the fatty acid induced death of malaria parasites is not clear at present. However, striking alterations in lipid metabolism have been reported in malaria-infected RBC. The usually low lipid metabolism of RBC rises sharply after invasion and throughout maturation of the parasite (7, 8). RBC harbouring mature schizonts, for example, are known to contain 3–5 fold more phospholipids than normal RBC (8). Incorporation of required ingredients by pinocytosis or through the RBC membrane pores is markedly higher in malaria-infected RBC than in normal RBC (9). As the parasite is devoid of de novo synthesis of fatty acids (7, 8), the infected RBC may take up fatty acids with great avidity. It is possible that this sudden influx of fatty acids, their methyl esters or oxidized fatty acids may be toxic to the parasite, although the basis for the toxicity probably differs according to the agent. Our morphological studies (see FIG. 8) showed that the fatty acids induced death of the parasite, and later these dead parasites moved to the exterior from the RBC via the parasitophorous vacuole orifice. Although we do not wish to be bound by preliminary speculations, this observation may suggest that the site of merozoite invasion, which acts as the orifice of the parasitophorous vacuole, has been damaged by the fatty acids or by their derivatives.

The toxicity of fatty acids for parasites probably occurs at a number of levels and involves their oxidized derivatives. In the case of extracellular parasites or the extracellular life cycle stage of a parasite, the lipid may act directly on the parasite membrane, affecting its normal function. For intracellular and intraerythrocytic parasites such as malaria, the lipids may affect the normal function of the parasite by acting on the host cell membrane (the host cell being the erythrocyte, hepatocyte, mononuclear phagocyte, muscle cell, lymphocyte etc). The action of lipids may either lead to toxicity of the host cells, which could then limit the replication of the parasite (eg as may occur for virus-infected cells), but in addition the lipids (at lower concentrations) may affect host cell scavenging systems which protect very sensitive parasites against oxidative damage. This could include systems which lead to the generation of reduced glutathione. Factors such as the concentration of the PUFA, the type of parasite and the specific stage of the parasite life cycle could determine which of the above three possibilities occurs.

It is evident from our studies that oxidized fatty acids are particularly effective in inducing parasiticidal effects of *P. falciparum* (see FIG. 6). It is likely as well that the effect of the parent non-oxidized fatty acid is related to its oxidation by the parasite or RBC, which constitute a highly oxidative environment (containing iron and high concentrations of oxygen). As might be expected if the oxidized species is the active form of the PUFA, antioxidants (such as BHT and Vitamin E) markedly reduce the anti-malarial activity of the fatty acids. Moreover, saturated and monosaturated fatty acids, which are more resistant to oxidative attack, are much less effective than fatty acids with two or more double bonds (see FIG. 3). As yet, the nature of the oxidation products which induce the effect remains unclear. Lipid hydroperoxy derivatives (mainly mono- and di-hydroxy derivatives) are major products of auto-oxidation, although a variety of other products (including alkanals, hydroxyalkanals, malonaldehyde, polymerised polar products, and even volatile carbonyl compounds) are produced as well (10). Whether some or all of these products are effective at inducing degeneration of the parasite remains to be determined. The mechanism of action of the active agents is clearly dependent on their structure. Thus, although we do not wish to be bound by preliminary speculations, hydroperoxy derivatives of fatty acids may act by oxidizing reduced glutathione and thereby making the parasite more susceptible to oxidative stress, while malonaldehyde is thought to interfere with membrane function through its ability to form cross linkages between proteins and lipids (11).

Although the mechanism of action is not entirely clear, at this stage, we believe that fatty acids (such as docosahexaenoic acid) can act either directly on the parasites, or indirectly by activating neutrophils (12) for increased killing of malarial parasites. Macrophages and neutrophils have been shown to be important effector cells against Plasmodium species (3, 4, 11, 13, 14, 15). Our findings suggest that polyunsaturated fatty acids (such as arachidonic acid) could be mediators of the effects of these phagocytic cells since these leukocytes are known to release arachidonic acid following stimulation (16, 17).

Antimalarial activity of fish oil was found to be relatively low (see Example 1B). Fish oils are a source of triglycerides containing omega-3 fatty acids, and the preparation used in Example 1B contained 18% $C_{20:5, n-3}$ and 12% $C_{22:6, n-3}$. It is possible that the remaining constituents of the fish oil counteracted the effects of the PUFA. Alternatively, the triglycerides containing the PUFA may not have been available to the parasite, because of the relatively larger size of the molecule.

The polyunsaturated fatty acids of the present invention can either be administered in the form of a pharmaceutical or veterinary composition, or in the form of a dietary supplement. Parenteral administration, e.g. by intraperitoneal administration or intravenous infusion, gives the best results, but oral administration is also possible.

REFERENCES

1. Anon. Malaria. In: Tropical Diseases Progress in International Research, 1987–1988. Ninth Programme Report, UNDP/World Bank/WHO, Geneva (1989), pp. 43–49.
2. Stevenson M. M. Preface In: Stevenson M. M., ed. Malaria: Host Responses to Infection. CRC Press, Inc., Boca Raton, Fla. (1990).
3. Kumaratilake L. M., Ferrante A., Rzepczyk C. M. Tumor necrosis factor enhances neutrophil-mediated killing of *Plasmodium falciparum*. *Infect Immun* (1990) 58:788–793.
4. Kumaratilake L. M., Ferrante A., Rzepczyk C. M. The role of T lymphocytes in immunity to *Plasmodium falciparum*: enhancement of neutrophil-mediated parasite killing by lymphotoxin and interferon gamma, comparisons with tumor necrosis factor effects. *J Immunol* (1991) 146:762–767.
5. Kim R. S., LaBella F. S. Comparison of analytical methods for monitoring antioxidation profiles of authentic lipids. *J Lip Res* (1987) 28:1110–1117.
6. Trager W., Jensen J. B. Human malaria parasites in continuous culture. *Science* (1976) 193:673–675.
7. Holz G. G. Jr. Lipids and the malarial parasite. Bulletin WHO (1977) 55:2–3.
8. Sherman I. W. *Biochemistry of Plasmodium* (malarial parasites). *Microbiol Rev* (1979) 43:453–495.
9. Burns E., Pollack S. *P. falciparum* infected erythrocytes are capable of endocytosis. *In Vitro Cellular and Develop Biol* (1988) 24:481–486.
10. Esterbauer H, Cheeseman K. H., Dianzani M. V., Poli G., Slater T. F. Separation and characterization of the aldehyde products of lipid peroxidation stimulated by ADP-$Fe^{2+}$ in rat liver microsomes. *Biochem J* (1982) 208:129–140.
11. Allison A. C., Eugui E. The role of cell-mediated immune responses in resistance to malaria, with special reference to oxidant stress. *Annu Rev Immunol* (1983) 1:361–32.
12. Poulos A., Robinson B. S., Ferrante A., Harvey D. P., Hardy S. J., Murray A. W. Effect of 22 to 32 carbon n-3 polyunsaturated fatty acids on superoxide formation in human neutrophils. Synergism of docosahexaenoic acid with phorbol myristate acetate and f-met-leu-phe. *Immunol* (1991) 73:102–108.
13. Taliaferro W. H., Taliaferro L. G. The effect of immunity on the asexual reproduction of *Plasmodium brasilianum*. *J Infect Dis* (1944) 75:1–32.
14. Jensen J. B. Malaria crisis forms, intraerythrocytic development derangement. In: Malaria: Host Responses to Infection. CRC Press, Inc., Boca Raton, Fla. (1990) pp. 109–127.
15. Ferrante A., Kumaratilake L. M., Rzepczyk C. M., Dayer J-M. Killing of *Plasmodium falciparum* by cytokine activated effector cells (neutrophils and macrophages). *Immunol Letters* (1990) 25:179–88.
16. DiPersio J. F., Billing P., Williams R., Gasson J. C. Human granulocyte-macrophage colony-stimulating factor and other cytokines prime human neutrophils for enhanced arachidonic acid release and leukotriene $B_4$ synthesis. *J. Immunol* (1988) 140:4315–4322.
17. Hope W. C., Patel B. J., Fiedler-Nagy C., Wittreich. Retinoids inhibit phospholipase $A_2$ in human synovial fluid and arachidonic acid release from rat peritoneal macrophages. *Inflam* (1990) 14:543–561.

See also Kumaratilake L. M., Robinson B. S., Ferrante A., Poulos A. Antimicrobial Properties of n-3 and n-6 Polyunsaturated Fatty Acids: In Vitro Effects on *Plasmodium falciparum* and In Vivo Effects on *P. berghei*. *J Clin Invest* (1992) 89:961–967.

The claims defining the invention are as follows:

1. A method of preventing or treating *Plasmodium falciparum* infection, trypanosomiasis, leishmaniasis, amoebiasis, trichomoniasis, primary amoebic meningitis, chronic acanthamoebic encephalitis and keratitis, babesiosis, or a disease caused by a nematode, trematode or cestode in a subject, comprising administering to the subject a fatty acid having a chain length of up 30 carbon atoms, and two or more double and/or triple bonds, an alcohol or amide derivative thereof or oxidation product.

2. A method according claim 1, wherein said fatty acid comprises two or more double bonds.

3. A method according to claim 2, wherein said fatty acid comprises 2 to 6 double bonds.

4. A method according to claim 3, wherein said fatty acid comprises 15 to 15 carbon atoms.

5. A method according to claim 4, wherein said fatty acid is n-1 linolenic acid, arachidonic acid, eicosapentaenoic acid or docosahexaenoic acid.

6. A method according to claim 1, wherein said fatty acid is an n-1 to n-10 fatty acid.

7. A method according to claim 6, wherein said fatty acid is an n-3 to n-6 fatty acid.

8. A method according to claim 7, wherein the fatty acid is an n-3 fatty acid.

9. A method according to claim 1, wherein said derivative is an alcohol or amide.

10. A method according to claim 1, wherein said oxidation product is a hydroxy fatty acid, hydroxy alkanal, hydroperoxy or endoperoxide derivative, malonaldehyde, or malondialdehyde.

11. A method according to claim 10, wherein said oxidation product is a hydroperoxy derivative.

12. A method according to claim 1, wherein the fatty acid is administered parenterally.

13. A method according to claim 1, wherein the disease being prevented or treated is *Plasmodium falciparum* infection, amoebiasis or trypanosomiasis.

14. A method according to claim 13, wherein the disease being prevented or treated is *Plasmodium falciparum* infection.

15. A method of treating melanoma tumors or a disease caused by bacteria, fungi, Chlamydia, Mycoplasma, Rickettsia or viruses in a subject, comprising administering to the subject an oxidized fatty acid having a chain length of up to 30 carbon atoms, and two or more double and/or triple bonds, or an alcohol or amide derivative thereof.

16. A method according to claim 15, wherein said fatty acid comprises two or more double bonds.

17. A method according to claim 16, wherein said fatty acid comprises two to six double bonds.

18. A method according to claim 15, wherein said fatty acid comprises 15 to 25 carbon atoms.

19. A method according to claim 18, wherein said fatty acid is linolenic acid, arachidonic acid, eicosapentaenoic acid or docosahexaenoic acid.

20. A method according to claim 15, wherein said fatty acid is an n-1 to n-10 fatty acid.

21. A method according to claim 20, wherein said fatty acid is an n-3 to n-6 fatty acid.

22. A method according to claim 21, wherein the fatty acid is an n-3 fatty acid.

23. A method according to claim 15, wherein said derivative is an alcohol or amide.

24. A method according to claim 15, wherein said oxidation product is a hydroxy fatty acid, hydroxy alkanal, hydroperoxy or endoperoxide derivative, malonaldehyde, or malondialdehyde.

25. A method according to claim 24, wherein said oxidation product is a hydroperoxy derivative.

26. A method according to claim 15, wherein the fatty acid is administered parenterally.

* * * * *

UNITED STATES PATENT AND TRADEMARK OFFICE
CERTIFICATE OF CORRECTION

PATENT NO.   : 5,604,258
DATED        : February 18, 1997
INVENTOR(S)  : FERRANTE et al It is certified that error appears in the above-identified patent and that said letters patent is hereby corrected as shown below:

Claim 4, line 2, delete "15 to 15" and replace by --15 to 25--.

Signed and Sealed this

Fourth Day of November, 1997

Attest:

BRUCE LEHMAN

Attesting Officer

Commissioner of Patents and Trademarks